United States Patent [19]

Neale et al.

[11] 4,348,114
[45] Sep. 7, 1982

[54] METHOD OF INSPECTING COATED WEB MATERIAL TO DETECT THE PRESENCE OF DOWNLINES THEREON

[75] Inventors: Denis M. Neale, Brentwood; Frederick J. Bontoft, Chelmsford; John B. Ikin, Leigh-on-Sea, all of England

[73] Assignee: Ciba-Geigy AG, Basel, Switzerland

[21] Appl. No.: 211,159

[22] Filed: Nov. 28, 1980

[30] Foreign Application Priority Data

Dec. 7, 1979 [GB] United Kingdom ............... 7942268

[51] Int. Cl.³ ............................................ G01N 21/17
[52] U.S. Cl. ................................... 356/431; 250/563
[58] Field of Search ...................... 356/429, 430, 431; 250/571, 572, 562, 563

[56] References Cited

U.S. PATENT DOCUMENTS

| | | | |
|---|---|---|---|
| 3,541,340 | 11/1970 | Binks | 250/562 |
| 3,556,664 | 1/1971 | Blaisdell et al. | 356/200 |
| 3,618,063 | 11/1971 | Johnson | 250/563 |
| 3,898,469 | 8/1975 | Nichols et al. | 356/430 |
| 4,005,281 | 1/1977 | Faulhaber et al. | 235/151.3 |
| 4,048,510 | 9/1977 | Clarke et al. | 356/430 |
| 4,118,127 | 10/1978 | Klein et al. | 356/200 |
| 4,274,748 | 6/1981 | Burtin et al. | 356/431 |

FOREIGN PATENT DOCUMENTS

| | | |
|---|---|---|
| 8010 | 2/1980 | European Pat. Off. |
| 1526375 | 9/1978 | United Kingdom |

*Primary Examiner*—R. A. Rosenberger
*Attorney, Agent, or Firm*—Harry Falber

[57] ABSTRACT

This invention relates to a method of inspecting coated web material in order to detect the presence of downlines. The coated web material is transported past an inspection station and is inspected transversely point by point across the web width. Data signals are produced responsive to variations in coated thickness. The inspection operation is repeated as the web pass the inspection station and the data signals from points at the same distance across the web width are summed to produce an average signal waveform. Any abnormal excursions of the averaged signal waveform are registered as faults.

7 Claims, 24 Drawing Figures

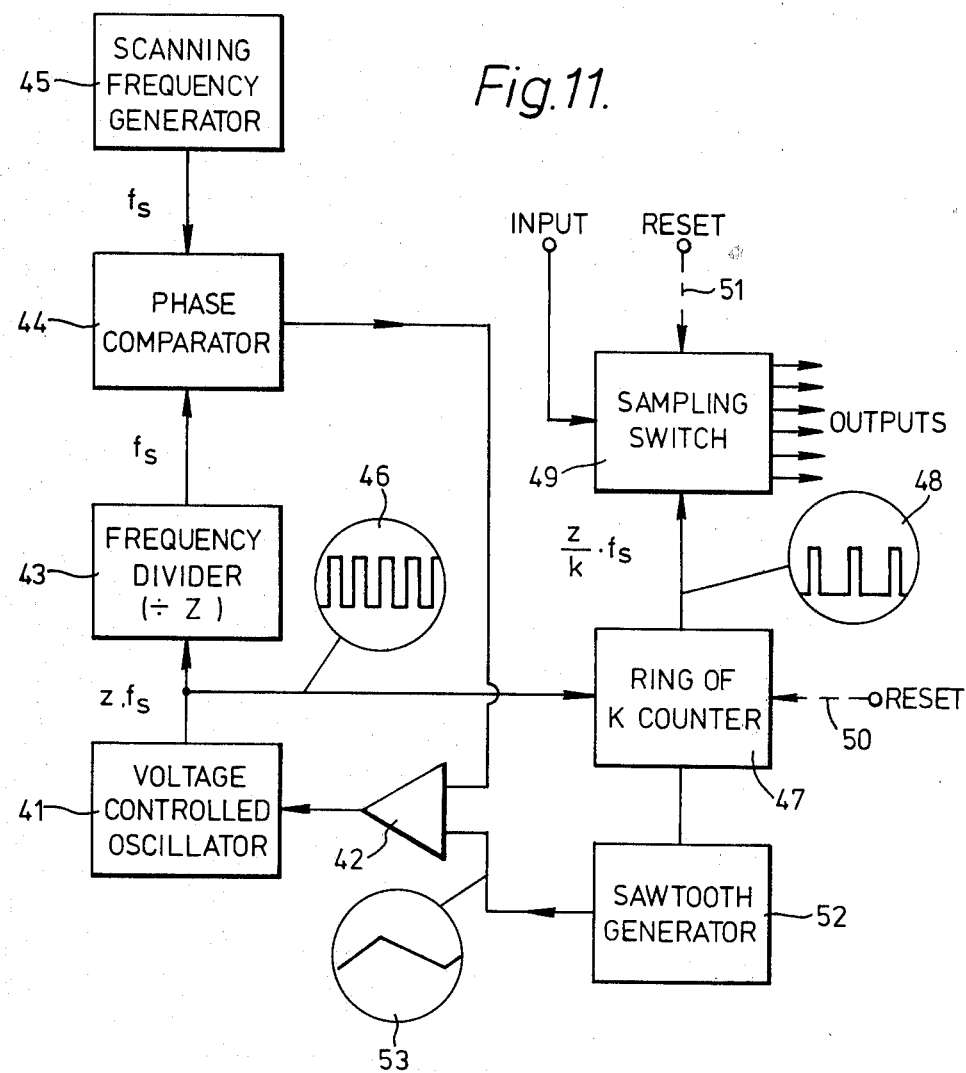

METHOD OF INSPECTING COATED WEB MATERIAL TO DETECT THE PRESENCE OF DOWNLINES THEREON

This invention relates to the inspection of coated web material.

In the manufacture of photographic films and papers, a very high degree of uniformity is sought during the coating of the silver halide-containing solutions onto the base material. In particular, great care must be exercised to ensure that the quantity of coating solution applied by the coating device varies by less than 2% from point to point across the coated width of the base web. If a local variation occurs exceeding this limit, it will be visible in the photographic material, after exposure and processing, as a streak running down the length of the web. Hereafter such streaks will be referred to as "downlines".

It has been recognised that the detectability of a downline increases with the length of web submitted to inspection. To detect very subtle downlines it may therefore be necessary to inspect a considerable length of web. This will necessarily delay indication of the presence of such a downline. Its detection is nevertheless important since, once initiated by contamination or damage to the coating device, a downline fault seldom removes itself spontaneously.

Downlines in coatings are particularly difficult to detect during manufacture for several reasons:
(1) The visibility of a downline is much less before the film or paper has been subjected to the amplification provided by chemical processing.
(2) Because the material is sensitive to visible light, visual inspection of the newly coated web is precluded or must be restricted to such a low light level as to be ineffective.
(3) Automatic inspection means generally examine the product point by point. The presence of a downline is then often concealed by random local variations in optical properties due to web structure and coating mottle. These random variations may be acceptable in a product whereas a downline of smaller peak amplitude may not be acceptable.

Thus there is a need for a method of examining coated webs so that downlines can be detected even at very low amplitudes.

Various attempts have been made to meet this requirement but hitherto they have all been of limited success because the fault signal is not readily detected in the presence of noise signals from web structure, coating mottle and electron noise in the inspection device. As the sensitivity to fault signals is increased, there is an increased probability of producing false indications in response to noise signals. Often, little can be done to separate the two by temporal filtering, because the frequency bands involved overlap.

It is known practice to scan the web repetitively and transversely with a beam shaped by optical means to be elongated in the direction of web movement. If, for example, the beam is thus spread to have a cross-section of length to width in the ratio 10 to 1, then a photocell receiving reflected or transmitted light delivers at each single scan a current waveform equivalent to that produced by averaging the waveforms of signals from 10 scans made with a square-section beam of the same width and arranged so that successive scans are contiguous and non-overlapping.

The value of such beam elongation is limited in practice by the following factors:
(1) The surface structure of the web and/or the mottle of the coating is generally coarse compared with the width of the scanning beam. Consequently there is a high degree of correlation between the web surface structure and mottle explored on one scan and on the next by a beam of square or circular cross-section. The noise components arising from the surface structure or mottle are therefore not independent and averaging of a few consecutive scans (e.g. by beam elongation) is able to provide only a limited improvement.
(2) There are severe practical difficulties in using a greatly elongated inspection beam. For example it would be difficult to provide and to maintain, in sufficiently good angular alignment with the web direction, an inspection beam with a cross-sectional length of 10 meters and a width of about 0.1 mm. Such a beam would call for angular alignment errors of less than 1 part in $10^5$.
(3) No reduction is provided in noise which may modulate the scanning beam before it falls on the web, nor in shot noise originating in the photocell.
(4) It is frequently required to detect, as well as any coating lines, the presence of small spots and pinholes in the web or its coating. Extending the length of the scanning beam cross-section to, say, 10 times its width then reduces by a factor of 10 the proportion by which the photocell current changes on crossing a circular defect of diameter equal to the width of the scanning beam. Elongating the beam does not per se produce a corresponding reduction in the amplitude of noise accompanying the signal, however. Consequently so far as the detection of spot defects is concerned, a reduction in signal/noise ratio will accompany any elongation of the cross-section of the scanning beam.

In the known art, methods have been devised which attempt to overcome the limitations listed above. These methods have depended on the electronic processing of signals obtained by scanning the web with a beam of circular or moderately elongated cross-section. The known methods are based on detection of coincidences in position of suspected fault signals produced when the web is repeatedly inspected transverse to the web direction.

For example one such system causes each suspected fault signal to open and close an electronic gate during the subsequent inspection. The gate is opened before the anticipated position of the fault is reached and is closed after it has been passed. If a signal is detected while the gate is open, a count is registered in a counter. When a predetermined number of counts has been accumulated on successive inspections, the downline is considered confirmed and its position may be recorded. This system can be effective in resisting false indications due to noise signals, but if the sensitivity is increased too far, noise signals can cancel or swamp small fault signals on individual inspections and accordingly the predetermined count is never reached.

If in an attempt to circumvent this problem, a lower number is chosen for the predetermined count, the risk is increased that a spurious indication of a downline will be produced by noise signals, which on successive inspections coincide with the open period of the electronic gate.

In one proprietary equipment, a two-stage system is used in an attempt to overcome this danger. Electronic gates and counters are used, as described already, to identify positions of possible downlines. Each time a predetermined count is reached by such a primary counter an impulse is fed to a secondary counter. If the secondary counter receives an appropriate number of impulses in a prescribed time, a downline is recorded. The improvement achieved derives from the ability of this two-stage system to identify the position of a line, the amplitude of which is close to that of accompanying noise signals and occasionally swamped by them.

All the known systems of downline detection suffer from the limitation that on individual inspections they require a fault signal to be detectably greater than the accompanying noise signals. Since noise signals are of indefinite amplitude, the maximum sensitivity to which the detector can usefully be set depends on the number of false indications which can be tolerated. Even with the two-stage system just described, however, reliable detection of a downline cannot be performed if the amplitude of the fault signal is less than about half the peak amplitude of the accompanying noise signals.

However it appears that the prior art makes insufficient use of those properties peculiar to a downline. For example, one of these properties is that a downline may be clearly visible in a sheet of coated paper measuring 1 meter square although invisible in any 1 cm strip cut transversely to the direction of the downline. This is because the surface texture of the paper provides visual information obscuring the presence of a subtle line fault. When viewing the 1 meter square sheet, however, the observer's brain can detect in the surface texture information a correlation which betrays the presence of the line fault.

To detect downlines at very low amplitude it is important to use so far as practicable all the data available both across the web width and down the length examined. There has been discovered a method which makes use of a high proportion of such data whilst reducing the cost and complexity of apparatus needed to implement full examination of the coated web.

According to the present invention there is provided a method of inspecting coated web material to detect the presence of downlines thereon which comprises passing the coated web material past an inspection point and inspecting the web transversely point by point across the web width to produce data signals responsive to variations in coated thickness, performing said transverse inspection repeatedly as the web moves past said inspection station, summing those parts of successive data signals corresponding to a first pattern of at least 100 points spaced at like distances across the web width, thereby producing an averaged signal waveform, detecting as faults any abnormal excursions of the averaged signal waveform occurring within a predetermined time and thereafter repeating said summing and detecting in respect of at least a second pattern of similarly spaced-apart points intermediate the spaced-apart points of said first pattern.

Thus in this method use is made of the known characteristic that the downline runs precisely parallel to the direction of web at the coating zone. This means that if the web is subsequently inspected by a succession of transverse scans made at constant frequency of repetition the fault signals will comprise signals at precisely the frequency of scanning and its harmonics. Moreover the fault signals will be in constant phase relation to the frequency of web scanning.

In a preferred form of the invention said summing and detecting is sequentially repeated in respect of at least 3 and not more than 16 patterns each of at least 100 similarly spaced-apart points, the points on each one pattern being intermediate the points on any other pattern.

In an alternative form of the invention the position of said first pattern is progressively moved between data signals so that within said predetermined time the said first pattern has been displaced no more than one-half the distance by which points in said pattern are spaced apart.

Depending on the means used to implement the invention there is usually a practical limit to the number of transverse inspections, the signals from which can usefully be summed. There is accordingly an advantage in arranging that each transverse inspection shall be made using an inspection aperture elongated in the web direction. In this way the data signal produced at any instant corresponds to the sum of data signals which would be generated by inspecting separately a number of points equidistant from the web margin but disposed a few millimeters along the web width. Data signals acquired using such an aperture may however be summed over a web length of 10 meters or more and there is therefore a practical advantage in combining the two techniques.

It is to be understood that the terms "summing" and "averaging" or "ensemble averaging" will herein be used interchangeably. Averaging comprises summing signals and attenuating the sum in proportion to the number of summations. The same result can be provided by attenuating the signals before summation, provided the number of summations is predetermined.

Summing of data signals produced by successive scans may be effected by known methods, for example by the use of a comb filter, a sampling filter, a charge-coupled delay line or a computer.

Thus in one form of the invention data signals produced by successive transverse inspections are sampled in respect of points across the web width and corresponding charges are fed in turn to storage capacitors corresponding in number to the number of said points, thereby to produce in the distribution of charges in the capacitors an analogue of the averaged signal waveform.

In a further form of the invention data signals produced by successive transverse inspections are sampled in respect of points across the web width and corresponding charges are fed serially into the input of a charge coupled delay line comprising M capacitors, the charge in said delay line being advanced from one capacitor to the next between sampling operations, the output of said delay line being connected to the input and the sampling operation being performed m times per transverse inspection, where M/m is an integer $\geq 1$, thereby to produce in the distribution of charges in the capacitors of the delay line an analogue of the averaged signal waveform.

In yet another form of the invention data signals produced by successive transverse inspections are sampled in respect of points across the web width, the result of each sampling operation being added to a value held in a computer store at an address corresponding to the distance across the web width corresponding to said sampling operation, thereby to produce in the stored values in the individual addresses a representation of the averaged signal waveform.

It is a characteristic of some downlines in coatings that the coating thickness is low in the centre of the line and high on either side of the line. The detectability of such a line is much greater if the width of the inspection beam is made no more than the width of the central, thinner part of the downline. Should a much wider inspection beam be used, the maximum excursion of the output signal from the photocell is the sum of light modulated simultaneously by the thicker and thinner parts of the downline. Accordingly it may be desirable to use a very narrow inspection beam and to divide the transverse inspection notionally into a large number of data points. The concurrent accumulation and analysis of data acquired from a large number of points can lead to complex and expensive hardware. To maintain sensitivity to narrow downlines and yet to reduce the complexity of hardware the invention provides that on any one transverse inspection only a selected proportion of the total number of points into which a transverse inspection is divided are sampled, data acquired on successive inspections using that selected proportion are analysed and thereafter the operation is repeated using a different selected proportion. This process is repeated until all positions across the web width have been examined for the presence of downlines.

According to a particular form of the invention, therefore, signals corresponding to successive transverse inspections at a scanning frequency are sampled at a frequency determined by a local oscillator controlled by a phase-locked loop to operate at a predetermined multiple of the scanning frequency, the signals being sampled over a time not exceeding half the period of oscillation of said local oscillator and the output of said local oscillator being phase modulated according to a cyclic pattern with respect to the scanning frequency so that the sampling operation explores alternative possible phase relations between said scanning signals and impulsive signals due to a downline.

In one form of said particular form the output of said local oscillator is phase modulated in step-wise manner.

In an alternative form of said particular form the output of said local oscillator is phase modulated according to a continuously varying function.

Practical embodiments of the invention will now be described with reference to the accompanying drawings in which:

FIG. 9 shows the arrangement of points on the web for which data is collected according to prior art.

FIG. 10 shows an arrangement of points on the web for which data is collected according to one form of the invention.

FIG. 11 shows in block schematic apparatus adapted to collection of data according to FIG. 10.

Figure 1:
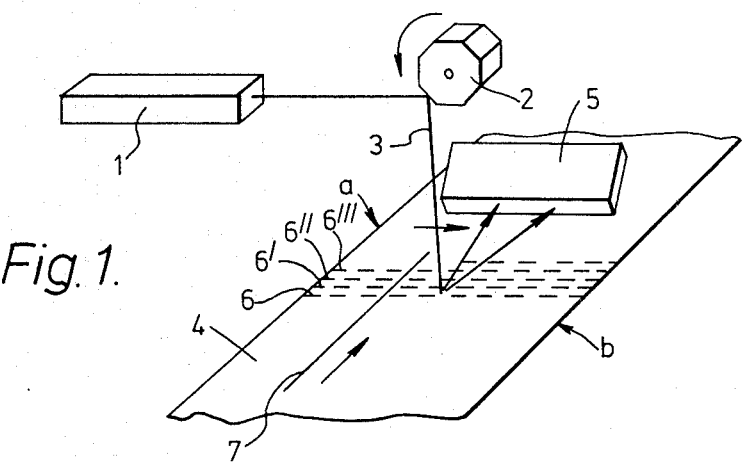
FIG. 1 shows a typical flying-spot laser scanner for web inspection according to the known art.
Figure 2A:
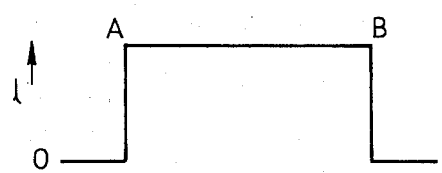
FIGS. 2a–2d show electrical waveforms relating to operations of the apparatus of FIG. 1 in hypothetical noise-free conditions.

In FIG. 1 a laser 1 projects a beam of light onto a rotating mirror polygon 2 so that the reflected beam 3 falls on a travelling web 4 and moves transversely across it. Light reflected from the web is received by a photocell in the housing 5 and gives rise to electrical signals indicative of the web reflectance and uniformity thereof. As the web moves continuously past the inspection station, which comprises the laser 1, the polygon 2 and the photocell cell housing 5, the repeated transverse movement of beam 3 causes the web to be inspected over a raster of parallel transverse paths represented in FIG. 1 by the broken lines 6, 6', 6'', 6''', etc. Ideally, inspection of a perfectly uniform coated web would cause the photocell to produce, in respect to each transverse inspection of the web, a electrical signal varying with time as shown in FIG. 2a. In FIG. 2a the photocell current, i, is shown as zero while the beam 3 is deflected beyond the edge of web 4. When beam 3 meets the edge a of the web, the light reflected from the web causes the photocell current to rise to a level dependent on web reflectance. The photocell current remains at this level, shown by the line AB in FIG. 2a, until the beam 3 leaves web 4 at edge b. Thereafter the photocell current falls abruptly to zero.

Figure 2B:
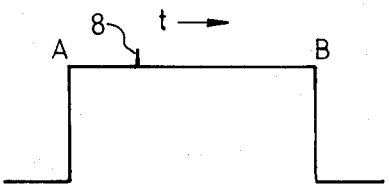

In moving across the web 4, beam 3 may encounter a line 7 of higher reflectance than average for the web material. This may be due, for example, to a line along which the coating is thin or absent. In such an event, the electrical signal shown in FIG. 2a would be modified to a form such as that shown in FIG. 2b. In FIG. 2b, the positive going pulse 8 in the photocell current is due to the momentary increase in current from the photocell as the beam 3 falls on line 7. Pulse 8 is readily detected by an electrical trigger circuit as a departure from the signal level established between points A and B.

Figure 2C:
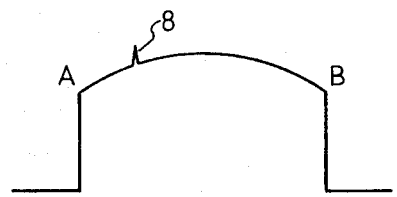
Figure 2D:
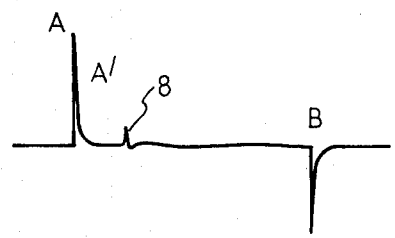

In a practical system, the line AB would probably be bowed as shown in FIG. 2c due to progressive changes in efficiency of collection of reflected light by the photocell as beam 3 scans across the web. However the narrow pulse 8 is readily distinguished from such relatively slow variations in the photocell current by temporal filtering. Whereas the bowing of line AB corresponds only to fundamental and low-order harmonics of the frequency of scanning of beam 3 across web 4, pulse 8 contains substantial energy in high-order harmonics of this frequency. Thus by filtering the signal to remove from it all frequencies corresponding to, say, the tenth harmonic and below, a waveform as shown in FIG. 2d may be obtained. A trigger circuit can then readily detect pulse 8 provided the trigger is gated to be active only between points $A^1$ and B in FIG. 2d, thereby excluding transient signals produced by beam 3 crossing web edges a and b.

The foregoing is well known to those concerned with web inspection systems. It is also well known that in a practical case the sensitivity to which the trigger circuit may be set is restricted by system noise. This noise arises from acceptable inhomogeneities in the web surface, perturbations in the laser beam and electron noise in the photocell. When photosensitive materials are to be inspected, the energy in beam 3 must be restricted to avoid significant exposure of the material. This restriction of beam energy means the photocell current can only be small and electron noise will be large in comparison. Accordingly in practice various noise components are superimposed on the waveforms shown in FIGS. 2a-2d and detection of a pulse 8 becomes difficult.

Figure 3A:
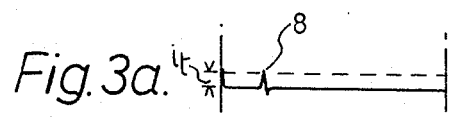
FIGS. 3a–3g show varying degrees of waveform degradation due to varying amplitudes of extraneous noise superimposed on the fault signal.
Figure 3B:
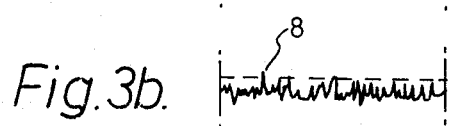

In FIG. 3a is shown that part of a noise-free signal corresponding to the section A'B in FIG. 2d. An electrical trigger circuit set to detect current impulses exceeding amplitude $i_t$ will readily detect pulse 8. When a small amount of noise is added to the signal waveform, as in FIG. 3b, pulse 8 can still be detected readily provided the amplitude of pulse 8 is greater than the amplitude of any excursions due to noise.

Figure 3C:
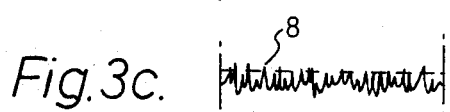

At a greater noise amplitude, as shown in FIG. 3c, the amplitude of pulse 8 is greater than most, but not all, noise excursions. Methods of dealing with this problem, according to the prior art, have been described above. They depend on using a trigger sensitivity sufficient to detect pulse 8 on an individual transverse scan of beam 3. Such a high sensitivity leads to tripping of the trigger by noise peaks of amplitude equal to or exceeding that of pulse 8. A comparison is made of the positions along the scan at which tripping of the trigger occurs on successive scans. Those which substantially coincide for a predetermined number of scans are deemed to correspond to line faults in the web.

Figure 3D:
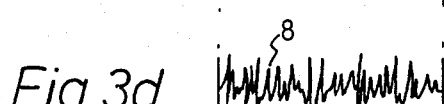
Figure 3E:
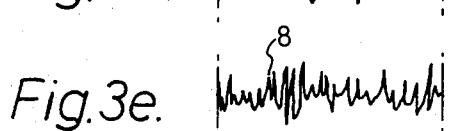
Figure 3F:
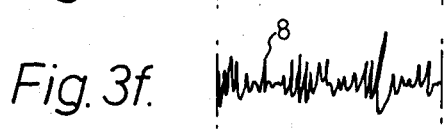
Figure 3G:
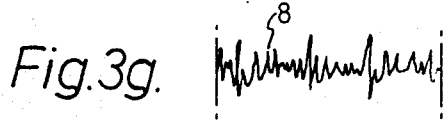

In FIG. 3d the superimposed noise is of still greater amplitude. In this case, pulse 8 is of smaller amplitude than the majority of noise peaks and on many scans the positive-going pulse 8 will be cancelled or reversed by chance coincidence of a negative-going noise peak. In the circumstances represented by FIG. 3d, such chance coincidences reduce the probability of tripping the trigger circuit on any one scan in response to pulse 8. On the other hand the probability increases of substantial coincidence of position of tripping on successive scans by noise peaks of amplitude greater than pulse 8. Line-detection methods according to the above-mentioned known art thus become reliable as the system noise becomes much greater than the amplitude of the signal to be detected.

Figure 4A:
FIGS. 4a–4d show the recovery of a signal from accompanying noise by use of ensemble averaging.
Figure 4B:
Figure 4C:
Figure 4D:
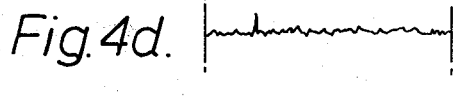

In the method according to the present invention no attempt is made to distinguish the fault signal from noise before the signals from a large number of scans have been combined. Referring to FIGS. 3d-3g, it will be seen that on successive scans across the moving web 4 the amplitude and phase of the fault signal 8 is always the same. The instantaneous amplitude of the noise components is unpredictable, however, and is sometimes above and sometimes below the average level represented by the waveform in FIG. 3a. Consequently if four or more waveforms are combined point to point along the scan the noise components will tend to cancel each other, but the fault signals 8 will reinforce each other. This process, known as "summation" or "ensemble averaging", is a known method of extracting signals buried in noise and use is made of it in performing the method of the present invention. If signals are combined by summation, the amptiude of the required pulse increaases in proportion to the number of signals combined. If signals are combined by averaging, the amplitude of the random noise component decreases in proportion to the square root of the number of signals combined. Thus by combining a sufficiently large number of scan waveforms, the noise component is reduced to a usefully small fraction of the amplitude of the fault signal. Thereafter the fault signal may readily be detected as described already with reference to FIGS. 3a and 3b. The effect of ensemble averaging is indicated in FIGS. 4a-4d. In FIG. 4a the fault signal 8 is submerged in noise, i.e. the ratio of signal current to noise current is less than unity. By combining signals from four separate scans of the web the signal/noise ratio is doubled, as shown at FIGS. 4b. FIGS. 4c and 4d show the further doublings of signal/noise ratio attainable by combining signals from 16 and 64 scans respectively. Ensemble averaging is a particularly powerful method of signal processing since there is no theoretical limit to the number of times the signal/noise ratio can be doubled, simply by quadrupling each time the number of independent scans, the signals from which are combined.

Figure 5:
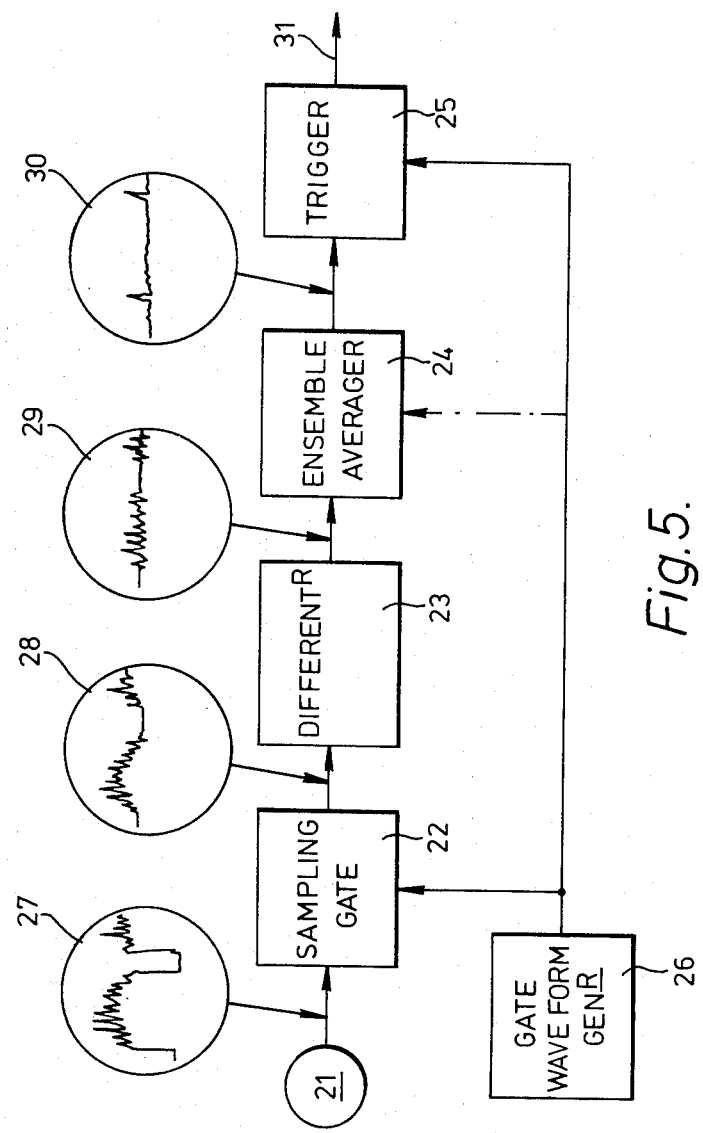
FIG. 5 shows in block schematic the signal processing system for identification of downline faults by use of an ensemble averager.

FIG. 5 shows how an ensemble averager may be applied to a web inspection system. In FIG. 5 the photocell 21 receives light transmitted by or reflected from the web. The current produced by the photocell has a substantially repetitive waveform shown inset at 27 and corresponding to FIG. 2c with the addition of random noise components. A gate waveform generator 26 is synchronised to the web scanning process and delivers to the sampling gate 22 gating signals causing gate 22 to exclude waveform disturbances due to passage of the scanning beam over the edges of the web (not shown here). Thus at the end of one scan when the scanning beam approaches the web edge b (FIG. 1) the signal level is maintained constant until the beam has crossed edge a at the start of the next scan. The modified signal waveform shown at inset 28 passes next to a differentiator 23. Essentially the differentiator is a high-pass filter which removes components at the scanning frequency $f_s$ and harmonics thereof up to about the tenth harmonic. Commonly the differentiator 23 may also attenuate very high frequencies, e.g. frequencies at or above 1000 times $f_s$. In such a case, the differentiator 23 may be described as a band-pass filter with a pass band from about 10 $f_s$ to 1000 $f_s$.

After differentiation the signal waveform is substantially as shown by inset 29. The impulse due to a downline may still be concealed by noise components. The ensemble averager 24 receives the waveform shown at 29 and, after receiving signals corresponding to many scans, produces an output waveform as shown at 30. The impulses due to a downline are now clearly distinguishable from the noise components because the latter have been averaged almost to zero. Waveform 30 is applied to a trigger circuit 25 adapted to detection of the major excursions of waveform 30. It may be desirable to cause the gate waveform form generator 26 to gate the trigger circuit so that triggering can occur only in response to signal disturbances produced during the active part of the scan, i.e. between crossing web edge a and leaving web edge b in FIG. 1. The output line 31 from the trigger can be used to operate an alarm when a downline is detected or to indicate its position on the web.

Having now described the application of averaging in web inspection, examples will be given of alternative ways in which the operation of ensemble averaging may be performed using the method of the present invention to effect economies in the associated apparatus.

If a Fourier analysis be made of repetitive waveforms shown in FIGS. 3d-3g, it will be found that the fault signal 8 gives rise to a spectrum of fixed frequencies corresponding to the frequency of scanning $f_s$ and integral harmonics thereof. For narrow downlines the harmonics involved will be of a high order and an aperiodic signal amplifier of adequate bandwidth will accept an undesirably wide band of noise signals. However, by filtering the composite signal to pass only the frequency of scanning and harmonics thereof, each with a very narrow bandwidth, the total bandwidth of the system can be greatly reduced. This means the energy of noise signals is correspondingly reduced without attenuating energy in the required fault signals. In this way the fault signal/noise ratio can be increased to exceed unity so that fault signals can be detected reliably even though they are initially accompanied by noise signals of much greater peak amplitude.

Figure 6A:
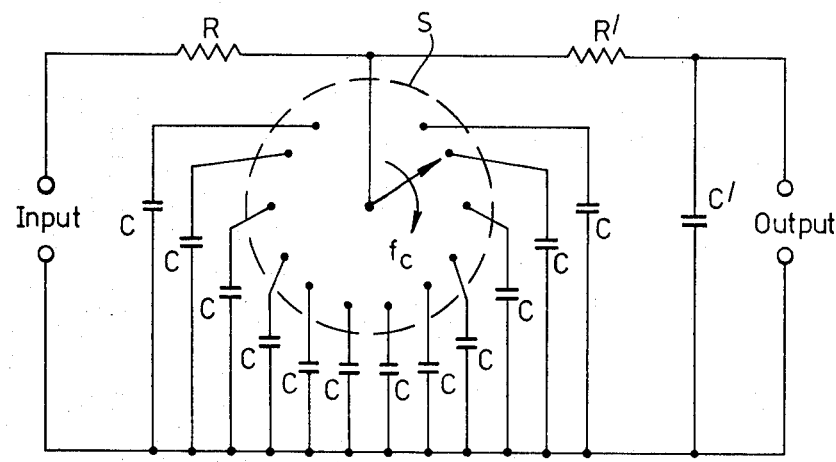
FIGS. 6a and 6b show two forms of a comb filter, known as a sampling filter.
Figure 6B:
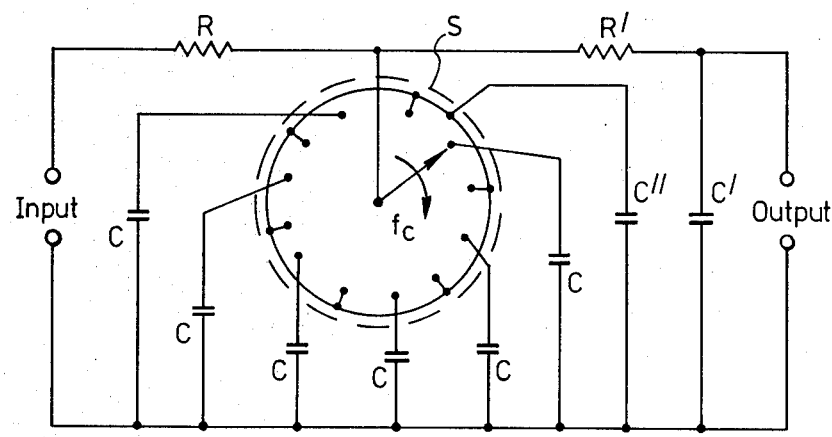

To achieve this narrow bandwidth it is necessary to have in the filter some form of energy storage with very low energy dissipation. The energy fed to the filter is summed if the inputs at the harmonically related frequencies are applied always in the same phase. Noise components coinciding with these frequencies will be distributed randomly in phase and hence will tend to cancel over the duration of many web inspections. A filter designed to pass or reject a known signal frequency and its harmonics selectively is known as a comb filter. Two forms of such a filter are shown in FIGS. 6a and 6b. This type of filter is known also as a sampling filter. It can readily provide very high values of Q and only practical convenience limits the order of harmonic frequencies which can be transmitted. It can therefore be used advantageously as the ensemble averager 24 in FIG. 5. This type of filter has been described in detail by W. R. Harden ("Electronics", July 24, 1867, pp. 91-100).

As shown in FIGS. 6a and 6b, a form of high-Q comb filter is produced by cyclically switching N alternative capacitors into a simple low-pass filter. If the switch arm rotates at frequency $f_c$, the filter provides passbands at zero frequency, $f_c$ and at harmonics of $f_c$.

With any one capacitor connected, the low-pass filter may be considered as an integrator of time-constant $\tau = CR$. However, as each capacitor is in circuit for only 1/N of the cycle, the voltage on any capacitor effectively charges with a time-constant of $\tau' = NCR$.

If one applies to the filter an input signal at frequency $f_c$ or at a harmonic of $f_c$ any individual capacitor will be connected to the same segment of the signal each time it is switched into circuit. The voltage on each capacitor will thus approach the average value of that signal segment at a rate determined by the time-constant $\tau'$ of the filter.

Noise components at frequencies not harmonically related to $f_c$ will not be in synchronism with the switching process. Consequently they will tend to charge a capacitor on one cycle and to discharge it on another. By making NCR sufficiently large, a high degree of protection against noise is provided. Each pass band of the filter, if centred on a frequency $n.f_c$, has 3 dB points at $n.f_c \pm 1/(2\pi NCR)$. The effective Q at each pass band is thus $n.f_c \pi NCR$, where n is the order of the harmonic.

The output from a sampling filter approximates the complex cyclic input waveform in a sequence of N steps. The output will therefore contain spurious components at the frequency $NF_c$ and odd-order harmonics thereof. These are readily removed by a further low-pass filter R'C', in FIGS. 6a and 6b.

The amplitudes at which the frequencies $f_c, 2f_c, \ldots nf_c$ are transmitted are given by the value of the transmission coefficient $A_n$ at each such frequency, where $$A_n = \frac{\sin\left(\frac{n\pi}{N}\right)}{\left(\frac{n\pi}{N}\right)}$$

From this it can be seen that if $A_n$ is to approximate unity at high values of n it is necessary to make $N > 4n$. Thus a practical consideration can be the very large number N of capacitors needed if it is required to transmit harmonics up to, say, the 100th order. Harden describes a version of this filter using solid-state switching. Using integrated circuits, the provision and switching of many capacitors is not a serious difficulty. Preferably $f_c$ is made equal to $f_s$, but expense becomes an important consideration if very narrow lines are to be detected in the web coating.

For example, if it is necessary to detect lines 0.5 mm wide occurring anywhere across a web of width 1.5 m, the value of N required according to the known practice of FIG. 7a would be $1500 \pm 0.5 = 3000$ at least. According to the present invention, however, a smaller number of capacitors can be used, e.g., 1500, provided each is switched into circuit for a time not exceeding 1/3000th of the period of the complex cyclic input waveform. The 1500 capacitors are connected individually to the 1st, 3rd, 5th, 7th etc. positions of the switch S. The intermediate (2nd, 4th, 6th, 8th etc.) positions are connected together and to a single capacitor C, as shown in FIG. 6b. In operation, the arm of switch S is rotated at frequency $f_c$ until sufficient data have been accumulated to determine whether a signal due to a coating line has been fed into one of the 1500 capacitors. Thereafter the switch arm would be caused to rotate at frequency $f_c$, but in phase relation to the complex cyclic input waveform shifted by a time equal to 1/300th of the period of that waveform. Time is again allowed for sufficient data to accumulate to indicate whether a signal due to a coating line can be detected in this alternative phase relation. Thereafter, operation of switch arm S reversts to the original phase relation once more. Operation may continue indefinitely using the two phase relations in alternation.

Figure 7:
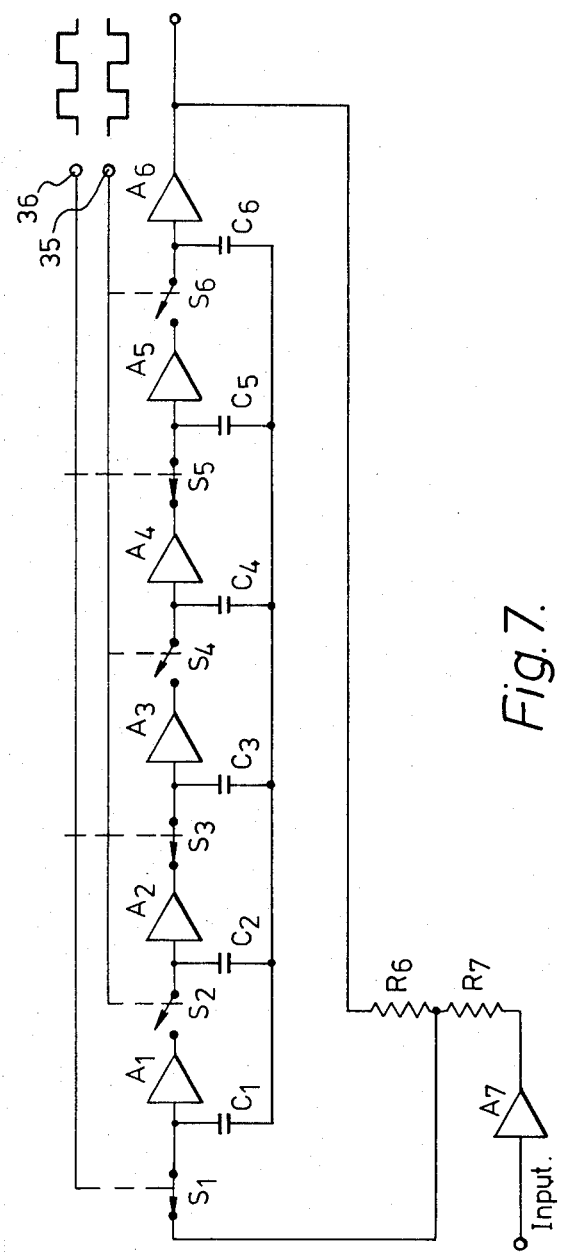
FIG. 7 shows a recursive delay line arranged to be used as an ensemble averager.

Yet another way of providing an ensemble averager is shown in FIG. 7. A number M of capacitors, here shown as $C_1$-$C_6$, are coupled to the respective inputs of unity-gain amplifiers $A_1$-$A_6$. Switches $S_1$-$S_6$ are arranged so that each capacitor can be connected to the output of the amplifier associated with the preceding capacitor. Thus when $S_3$ is closed, as shown, the voltage on $C_3$ becomes equal to that on $C_2$. All the odd-numbered switches close and open in sympathy and in synchronised anti-phase with the opening and closing of the even-numbered switches. Thus a line of M capacitors can store up to m/2 analogue voltages arranged in a pattern which is advanced by two capacitor positions towards the right of FIG. 7 each time the switches complete one cycle of their anti-phase switching operation.

By coupling the output of $A_6$ back to switch $S_1$, the line of capacitors is made recursive. Then a voltage pattern leaving the right hand end of the line is reintroduced at the left.

An input signal passing through amplifier $A_7$ may be combined with the signal delivered from amplifier $A_6$. The resistors $R_6$ and $R_7$ are proportioned so that $R_7 >> R_6$. Consequently, when $S_1$ is closed, the potential assumed by $C_1$ is determined primarily by the output of $A_6$ and only to a small extent by the output of $A_7$.

In use, as an ensemble averager 24 in FIG. 5, the switches are operated cyclically at a clock frequency $f_r$ chosen so that $f_r = M.f_s$. If the inspected web contains a downline, a signal pulse will be applied to the input of $A_7$ always in synchronism with the recycling of previously introduced pulses due to the same downline. If a plurality of downlines should occur on the same web, a corresponding pattern of voltages will be established on capacitors $C_1$–$C_6$ and circulated in synchronism with the frequency of scanning, $f_s$. Noise components applied to the input of $A_7$ will produce little immediate effect on the voltage on $C_1$. Also, because of their random phase relationship to the scanning frequency $f_s$, the noise components tend to integrate to zero over many recursions.

For a practical system, many more than six capacitors may be required. Charge transfer devices are now available as integrated circuits however, with 512 capacitors in line. The number of recursions which can usefully be made is limited by various leakage and crosstalk effects and may be about 100. For this reason it is advantageous to use this type of ensemble averager in combination with a scanning beam which is elongated in the web direction, as discussed above.

Charge transfer devices suitable for this application are manufactured by E. G. & G. Reticon, Sunnyvale, Calif., U.S.A., and are described in literature published by that company in 1978 and entitled "Product Summary: Discrete Time Analog Signal Processing Devices" and Application Notes No. 114 entitled "Charge Transfer Devices for Sampled-Data Processing".

As mentioned above, a line of M capacitors can store up to M/2 analogue voltages. Thus a device using 512 capacitors can sum or average data for only 256 elements across the width of a scanned web. Interleaved between these 256 elements are at least another 256 elements from which no data are accepted because switch $S_1$, in FIG. 7, is open at the instants at which they should be sampled. According to the invention, however, means are provided for sampling a different group of elements after every number, W, of scans where W is a number large enough to assure adequate improvement of signal/noise ratio by summing or ensemble averaging. In a simple embodiment, it is necessary only to interchange, after every W scans, the antiphase inputs applied to lines 35 and 36 in FIG. 7. This ensures tht the timing of operations of switches $S_1$ to $S_6$, whilst remaining synchronised to the scanning operation, becomes reversed so that an alternative pattern of elements is examined after each W scans.

In practice it has been found that even when drive waveforms of equal mark-space are applied to lines 35 and 36, the charge transfer delay line appears to be responsive to input signals occurring only during a part of the time during which $S_1$ should be effectively closed. This means that the 256 elements across the web width examined are narrower than otherwise expected and separated by a greater number of similar elements which are not examined. The invention includes a method of taking advantage of this possibility and an appropriate embodiment is described later with reference to FIGS. 10 and 11.

One more example of an ensemble averager will now be given, suitable for use in the system described in Brit. Pat. No. 1526375 and shown in FIG. 5. This last example uses a zero-crossing detector (ZCD) and a digital computer. The signal to be processed is applied to a ZCD which converts it to digital form, i.e. the ZCD delivers a "1" if the input is positive and an "0" when the input is negative. A clock pulse synchronised to an appropriate harmonic of the scanning frequency $f_s$ causes the computer to operate cyclically according to the outline flow-sheet shown in FIG. 8. At each cycle the computer removes a previously accumulated number from a particular address in a store. The ZCD output is added to this number and the sum is returned to the same address. The computer then awaits a further clock pulse before advancing to the next address in the store and repeating the operation.

If the clock frequency is Z times the scanning frequency $f_s$ a computer subroutine (not shown here) ensures that after Z such cycles the computer will return to the first address of the Z addresses used for accumulating data from the ZCD.

If the input to the ZCD contains only random noise unsynchronised to $f_s$ the Z addresses will each accumulate counts at an average rate corresponding to half the frequency of scanning. This follows because there will be an equal probability of an output from the ZCD being in a "1" or an "0" condition. At those instants corresponding to inspection of a downline, however, there will be a bias in the probability so that, for example, a "1" may be more often delivered than a "0" when a particular address is being updated. In this event, that particular address will accumulate significantly more counts than do the other stores.

Figure 8:
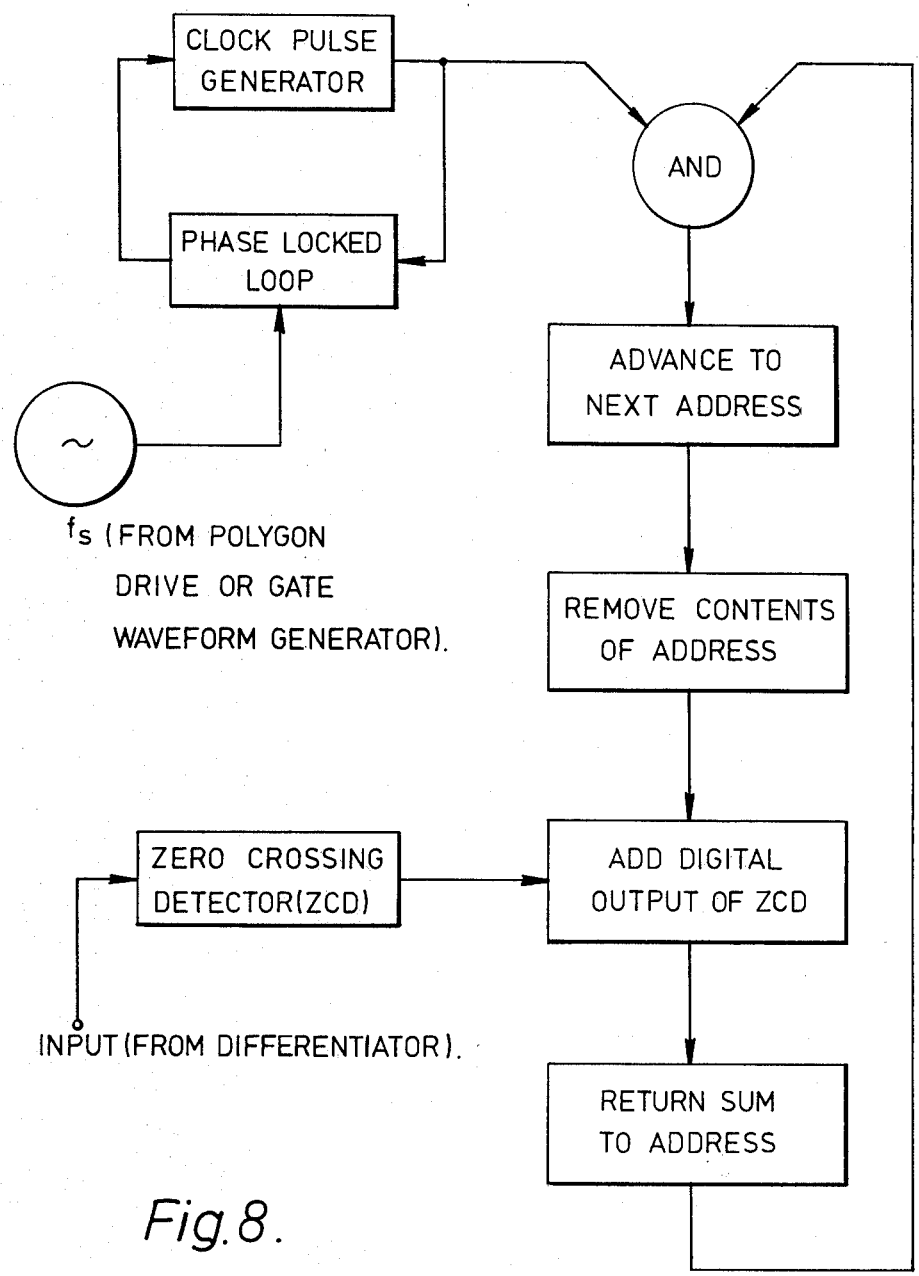
FIG. 8 illustrates the use of a zero-crossing detector with a digital computer to perform ensemble averaging.

After a predetermined number of cycles of operation according to the logic of FIG. 8, the computer examines the contents of the Z addresses and reports on the presence, severity and position of downlines, either directly or by operating the trigger 25 shown in FIG. 5.

There are, of course, many variations in detail to the way in which the computer may be used. For example, instead of adding a count in respect of "1" and no count in respect of "0", it may be preferred to add a count in respect of "1" and subtract a count in respect of "0". This mode of operation is then more closely analogous to other methods described already in that noise components integrate to zero rather than to a progressively increasing count. An advantage arising from the use of a computer in this way to perform ensemble averaging lies in the removal of any limitation on the number of scan waveforms which may be averaged. As it operates in a purely digital manner, the computer memory is not prone to loss of data by energy dissipation, e.g. by leakage of charge from capacitors. Consequently, by averaging data acquired over a very great web length, the computer can identify downline fault signals many times smaller than accompanying noise components.

In order to operate with sufficient speed it may be necessary to use special interface equipment to allow the computer to accept blocks of data at times suited to its own internal timing. Such equipment, known as a 'data break input' is familiar to those skilled in computer technology and will not be described here.

Even when such expedients are used, it may be difficult to operate a computer at such a speed that all available data is examined. Whether this is the case depends on the frequency of scanning $f_s$ and the number of points along the path of inspection which are to be examined.

Figures 9, 10:
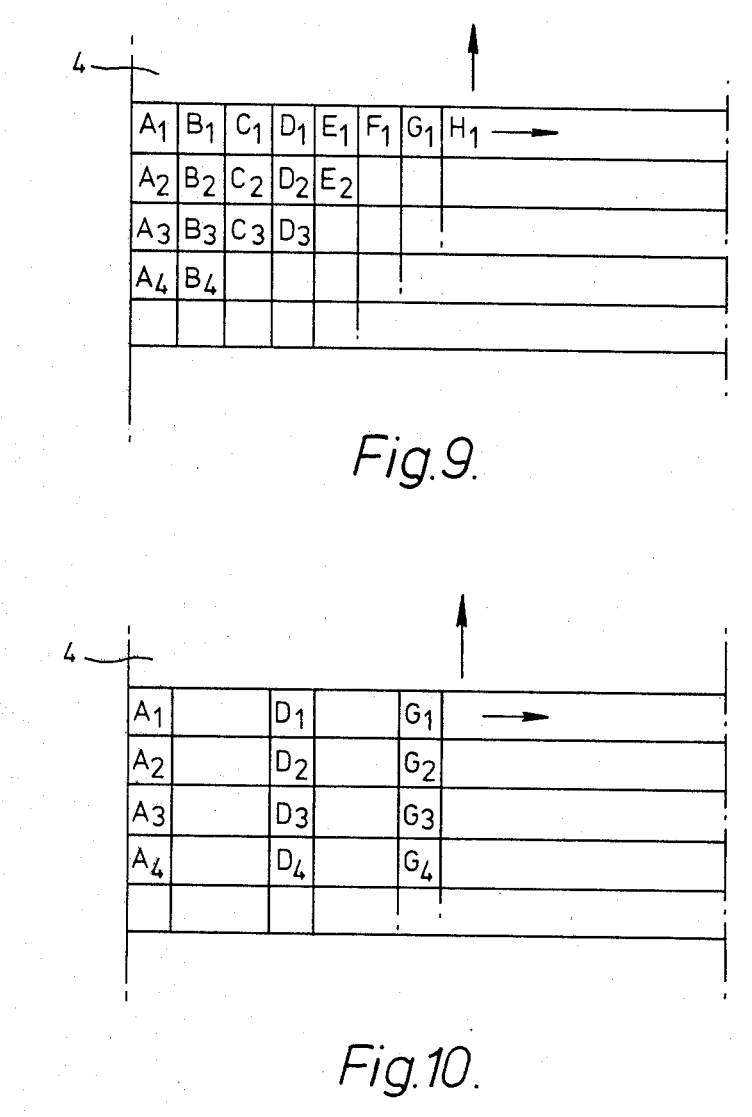

In the embodiment described so far with reference to FIG. 8, data may be analysed in respect of all notional elemental areas on the web 4. Referring to FIG. 9, the inspection beam may be considered to explore in turn, during a single transverse scan, the elemental areas $A_1$, $B_1$, $C_1$, $D_1$, $E_1$, $F_1$, $G_1$, $H_1$ etc. On the next scan the web will have advanced by a distance equal to the length of cross-section of the inspection beam. The inspection beam will therefore explore elemental areas $A_2$, $B_2$, $C_2$, $D_2$, $E_2$ etc., and, on succeeding inspection, areas $A_3$, $B_3$, $C_3$, $D_3$ etc.

As already described, ensemble averaging is carried out for areas $A_1$, $A_2$, $A_3$, $A_4$–simultaneously with separate ensemble averaging for areas $B_1$, $B_2$, $B_3$, $B_4$–and for each other column indicated by the latters C, D, E, F, G, H, and so on.

If downlines as narrow as 0.5 mm are to be found in a web 1.5 m wide, 3000 simultaneous ensemble averaging operations appear necessry. Provision for this would require an uneconomic amount of apparatus and an alternative form of apparatus is now described which uses the method of the present invention.

In FIG. 10 the photocell signals are sampled so that data are collected only in respect of elemental areas $A_1$, $D_1$, $G_1$, etc., on the first transverse insepection shown. On successive inspections data are collected at substantially the same points along the scan so that ensemble averaging may be performed on data from areas $A_1$, $A_2$, $A_3$, $A_4$,–and (separately) on data from areas $D_1$, $D_2$, $D_3$, $D_4$,–and $G_1$, $G_2$, $G_3$, $G_4$,–Because only every third elemental area is sampled in FIG. 10 this arrangement requires only one third as many simultaneous ensemble averaging operations as the arrangement shown in FIG. 9. This makes it possible to reduce correspondingly the complexity of the apparatus required or to reduce the speed at which a computer must operate to analyse the data in real time.

The arrangement shown in FIG. 10 would, of course, fail to detect a downline lying entirely between two neighbouring columns of sampled areas. For example, a downline lying along column B and/or column C would not be detected so long as only columns A, D, G, etc., were sampled. To overcome this limitation it is necessary to cyclically move the position of sampling so that alternative possible positions for a downline are explored. Thus, when data from sufficient scans have been ensemble averaged with the sampling pattern A, D, G, etc., of FIG. 10, the sampling pattern would be changed to B, E, H, etc., for further ensemble averaging. After this, the whole cycle of operations may be repeated again.

Whereas the invention provides for a useful reduction in the number of data storage elements required to permit identification of a narrow, randomly-placed, downline, the method of the invention implies a corresponding increase in the total number of scans required to inspect the web for a line or lines in all possible positions. Consequently, although FIG. 10 shows an embodiment in which every third element is examined on any one scan, greatly reduced sampling densities are not generally attractive. In some applications, every fourth or every fifth element might well be examined. It is unlikely, however, that an advantage would be found in sampling less frequently than every sixteenth element since the overall web inspection operation would then take 16 times as long as known practice based on sampling each element on every scan.

Progression of the sampling pattern from one phase relation with the scanning frequency to another may be performed step-wise as described above. Alternatively, provided the phase relation is changed sufficiently slowly, the progression may be performed continuously. A sufficiently slow progression is one in which the phase relation changes by the equivalent of half the width of an elemental area during the number of scans over which ensemble averaging is necessary to separate the downline signal from accompanying noise.

FIG. 11 shows schematically apparatus for implementing the proposal described with reference to FIG. 10. In FIG. 11, the local oscillator 41 operates at a frequency controlled by the voltage applied to its input by amplifier 42. The output of oscillator 41 is divided in frequency by an integral factor Z in the frequency divider 43. In normal operation the result of this frequency division is an output at the scanning frequency $f_s$. The phase comparator 44 compares the phases of the outputs of the frequency divider 43 and the scanning frequency generator 45, both of which are at frequency $f_s$. The phase comparator produces a voltage output which is applied to one input of amplifier 42 and causes the output voltage to oscillator 41 to be adjusted in a sense opposing any progressive drift in phase between the two inputs to phase comparator 44. Items 42, 41, 43, 44 thus comprise a phase-lock loop causing oscillator 41 to operate at a frequency Z times that of $f_s$.

The output of oscillator 41 is conveniently of rectangular waveform as shown at inset 46. This waveform is fed to a ring of K counter 47 which delivers only one positive-going output pulse for every K input pulses received from oscilltor 41. The output of counter 47 is shown at inset 48 and is applied to a solid-state sampling switch 49 which is analogous to rotary switch S in FIG. 6, for example. During the time the output of counter 47 is positive switch S may be considered closed to one of the switch contacts shown in FIG. 6a. While the output of counter 47 is zero or negative, the arm of switch S may be considered to be in a position intermediate between two successive contacts.

If oscillator 41 delivers an output of equal mark/space ratio and if K=2, the switch 49 will be closed to one output line at a time for only 25% of the total operating time. At each positive-going output from counter 47 closure will be made to a different output, at least Z/K outputs being provided.

The input to switch 49 is the filtered signal shown at 29 in FIG. 5. The outputs of switch 49 may be connected to capacitors analogous to capacitors C shown in FIG. 6a.

As described so far, switch S samples signals relating to only 1 in 4 of Z notional elemental areas along the path of transverse scanning of the web. This means that, without sacrificing sensitivity to very narrow defects, the number of outputs required from switch 49 is reduced to one-quarter.

To ensure that the sampling operation proceeds according to the same pattern on each successive scan, synchronising signals are applied to Reset lines 50 and 51 connected to counter 47 and sampling switch 49. The synchronising signals may, for example, be generated by the step in photocell output current produced when scanning beam 3 in FIG. 1 crosses web edge a.

To ensure that no downline escapes detection because it is hidden between sampling points, a sawtooth generator 52 feeds a slowly varying voltage into a second input of amplifier 42. Preferably this slowly varying voltage has a symmetrical waveform as shown at 53 in FIG. 11. The fundamental frequency of this symmetrical waveform may, for example, be such that one complete cycle corresponds to 4K.E cycles of the local oscillator 41, where E is the number of data points which must be ensemble averaged to raise a signal above noise.

Application of waveform 53 to amplifier 42 causes the phase of inputs to the comparator 44 to shift until a complementary waveform appears superimposed on the output of the comparator 44. By suitably adjusting the amplitude of waveform 53, it is arranged that the sampling waveform 48 changes very slowly in phase relative to the synchronising signal applied to reset lines 50 and 51. As a result, the positions across the web in respect of which the photocell output is sampled by switch 49 are changed progressively so that all possible positions for a downline are explored.

Because only one-quarter (for example) of the film width is being examined at any particular scan, it is necessary to examine a correspondingly increased length of web to be certain of detecting any downlines present.

Although the foregoing description refers to a symmetrical sawtooth waveform delivered by generator 52 in FIG. 11, it is to be understood that this waveform need not be symmetrical. It may also vary in amplitude in stepwise manner, i.e. by a waveform of staircase nature. It is preferable that the waveform should show equal probability for all its amplitude values and the symmetrical sawtooth waveform is preferred on grounds of practical simplicity and convenience.

The invention as described with reference to FIGS. 10 and 11 has made particular reference also to the method of sampling a signal shown in FIG. 6a. It is however to be understood that, by using a sampling switch providing a single output only, it is possible to apply the principle of cyclically phase-modulated sampling also to embodiments described with reference to FIGS. 7 and 8. In these cases the sampling switch would precede the input to the circuit shown in the relevant diagram.

Thus there has been developed a method which differs from prior art described above and in which prior art electronic gates are used to exclude part of the data available across the web width and counting circuits are used to reject groups of data acquired down the length of the web but not producing predetermined numbers of consecutive counts.

We claim:

1. A method of inspecting coated web material to detect the presence of downlines thereon which comprises passing the coated web material past an inspection station and inspecting the web transversely point by point across the web width to produce data signals responsive to variations in coated thickness, performing said transverse inspection repeatedly as the web moves past said inspection station, summing those parts of successive data signals corresponding to a first pattern of at least 100 points spaced at like distances across the web width, thereby producing an averaged signal waveform, detecting as faults any abnormal excursions of the averaged signal waveform occurring within a predetermined time and thereafter repeating said summing and detecting in respect of at least a second pattern of similarly spaced-apart points intermediate the spaced-apart points of said first pattern.

2. A method according to claim 1 in which said summing and detecting is sequentially repeated in respect of at least 3 and not more than 16 patterns each of at least 100 similarly spaced-apart points, the points on each one pattern being intermediate the points on any other pattern.

3. A method according to claim 1 in which the position of said first pattern is progressively moved between successive data signals so that within said predetermined time the said first pattern has been displaced no more than one-half the distance by which points in said pattern are spaced apart.

4. A method according to any one claims 1–3 wherein data signals produced by successive transverse inspections are sampled in respect of points across the web width and corresponding charges are fed in turn to storage capacitors corresponding in number to the number of said points, thereby to produce in the distribution of charges in the capacitors an analogue of the averaged signal waveform.

5. A method according to any of claims 1–3 wherein data signals produced by succcessive transverse inspections are sampled in respect of points across the web width and corresponding charges are fed serially into the input of a charge coupled delay line comprising M capacitors, the charges in said delay line being advanced from one capacitor to the next between sampling operations, the output of said delay line being connected to the input and the sampling operations being performed m times per transverse inspection, where M/m is an integer $>1$, thereby to produce in the distribution of charges in the capacitors of the delay line an analogue of the averaged signal waveform.

6. A method according to any of claims 1–3 wherein data signals produced by successive transverse inspections are sampled in respect of points across the web width, the result of each sampling operation being added to a value held in a computer store at an address corresponding to the distance across the web width corresponding to said sampling operation, thereby to produce in the stored values in the individual addresses a representation of the averaged signal waveform.

7. A method according to any of claims 1–3 wherein signals corresponding to successive transverse inspections at a scanning frequency are sampled at a frequency determined by a local oscillator controlled by a phase-locked loop to operate at a predetermined multiple of the scanning frequency, the signals being sampled over a time not exceeding half the period of oscillation of the local oscillator and the output of said local oscillator being phase modulated according to a cyclic pattern with respect to the scanning frequency so that the sampling operation explores alternative possible phase relations between said scanning signals and impulsive signals due to a downline.

* * * * *